United States Patent
AlSofi et al.

(10) Patent No.: US 11,761,874 B2
(45) Date of Patent: Sep. 19, 2023

(54) CMC-BASED METHOD FOR SURFACTANT CONCENTRATION DETERMINATION

(71) Applicant: SAUDI ARABIAN OIL COMPANY, Dhahran (SA)

(72) Inventors: Abdulkareem AlSofi, Dhahran (SA); Abdulaziz AlKhateeb, Al-Khobar (SA); Ziyad Kaidar, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 520 days.

(21) Appl. No.: 16/875,346

(22) Filed: May 15, 2020

(65) Prior Publication Data

US 2021/0356373 A1 Nov. 18, 2021

(51) Int. Cl.
*G01N 13/02* (2006.01)
*G01N 33/18* (2006.01)

(52) U.S. Cl.
CPC ............. *G01N 13/02* (2013.01); *G01N 33/18* (2013.01); *G01N 2013/0275* (2013.01); *G01N 2013/0283* (2013.01)

(58) Field of Classification Search
CPC .................. G01N 13/02; G01N 33/18; G01N 2013/0275; G01N 2013/0283
See application file for complete search history.

(56) References Cited

U.S. PATENT DOCUMENTS

| 5,710,048 A | 1/1998 | Ernst et al. |
| 7,888,128 B2 | 2/2011 | Geisler et al. |
| 2002/0054861 A1* | 5/2002 | Schmucker ............ A61K 8/442 424/70.1 |
| 2005/0037509 A1 | 2/2005 | Geisler et al. |

(Continued)

FOREIGN PATENT DOCUMENTS

| CN | 105115929 A | * 12/2015 |
| CN | 105181532 A | * 12/2015 |

(Continued)

OTHER PUBLICATIONS

CN-105181532-A-English (Year: 2015).*

(Continued)

*Primary Examiner* — Kristina M Deherrera
*Assistant Examiner* — Fatemeh Esfandiari Nia
(74) *Attorney, Agent, or Firm* — Osha Bergman Watanabe & Burton LLP

(57) ABSTRACT

A method includes determining a critical micelle concentration ($C_{cm\ assumed}$) of a sample with an unknown concentration ($C_s$) of a surfactant based on an assumed surfactant concentration ($C_{assumed}$) of the sample, providing a benchmark solution with a known concentration of the surfactant, determining an actual critical micelle concentration ($C_{cm}$) of the surfactant from the benchmark solution, and calculating the unknown concentration ($C_s$) of the surfactant in the sample from the following equation: $C_s = C_{cm}/(C_{cm\ assumed}/C_{assumed})$.

4 Claims, 7 Drawing Sheets

(56) References Cited

U.S. PATENT DOCUMENTS

2015/0275627 A1　10/2015　Xu et al.
2019/0094199 A1　　3/2019　Shi et al.
2022/0105123 A1*　4/2022　Ryu ..................... C12N 15/113

FOREIGN PATENT DOCUMENTS

| CN | 106092833 A | * | 11/2016 |
| EP | 1729109 A1 | | 12/2006 |
| EP | 2799866 A1 | | 11/2014 |
| SU | 828022 A1 | | 5/1981 |
| WO | 1999039196 A1 | | 8/1999 |

OTHER PUBLICATIONS

CN-105115929-A-English (Year: 2015).*
CN-106092833-A-English (Year: 2016).*
International Search Report and Written Opinion issued in Application No. PCT/US2020/035081, dated May 6, 2021 (19 pages).

* cited by examiner

CMC-BASED METHOD FOR SURFACTANT CONCENTRATION DETERMINATION

BACKGROUND

Surface active agents (surfactants) are generally amphiphilic organic compounds containing both a hydrophobic (water-insoluble) component and a hydrophilic (water-soluble) component. Surfactants may be classified according to the charge carried by the hydrophilic part of the molecule, e.g., as anionic, cationic, non-ionic or zwitterionic. The dual nature of surfactants favors their use in applications such as detergents, wetting agents, emulsifiers, or dispersants.

As surfactant concentration in an aqueous solution increases, the surfactant molecules may aggregate. A common surfactant aggregation is a micelle, where the hydrophilic portions of the surfactant may form a sphere-like shaped outer layer around a core of the hydrophobic portions of the surfactant clustered together.

Surfactant concentration in an aqueous solution is known to affect the surface tension of the aqueous solution. Accordingly, tools and procedures for measuring the surface tension of a surfactant-containing aqueous solution have been used to determine the concentration of the surfactant in such surfactant-containing aqueous solutions.

SUMMARY

In one aspect, embodiments disclosed herein relate to methods that include determining a critical micelle concentration ($C_{cm\ assumed}$) of a sample with an unknown concentration ($C_s$) of a surfactant based on an assumed surfactant concentration ($C_{assumed}$) of the sample, providing a benchmark solution with a known concentration of the surfactant, determining an actual critical micelle concentration ($C_{cm}$) of the surfactant from the benchmark solution, and calculating the unknown concentration ($C_s$) of the surfactant in the sample from the following equation: $C_s = C_{cm}/(C_{cm\ assumed}/C_{assumed})$.

In another aspect, embodiments disclosed herein relate to devices that include a sample fluid chamber, a benchmark solution chamber, a concentration fluid chamber, a flow path between the concentration fluid chamber and each of the sample fluid chamber and the benchmark solution chamber, a tensiometer positioned proximate the sample fluid chamber and the benchmark solution chamber, and a housing containing the sample fluid chamber, the benchmark solution chamber, and the tensiometer.

In yet another aspect, embodiments disclosed herein relate to devices that include a measurement device for measuring a physical property of a solution, the measurement device selected from a tensiometer, a spectrometer, and an electrical conductivity meter, a non-transitory computer readable medium storing instructions executable by a computer processor, and at least one input device connected to the computer processor. The instructions may have functionality for obtaining from the measurement device a plurality of physical property measurements of a sample with an unknown concentration ($C_s$) of a surfactant and of a benchmark solution with a known concentration of the surfactant, determining a critical micelle concentration ($C_{cm\ assumed}$) of the sample from the plurality of physical property measurements of the sample and based on an assumed surfactant concentration ($C_{assumed}$) of the sample, determining an actual critical micelle concentration ($C_{cm}$) of the surfactant in the benchmark solution from the plurality of physical property measurements of the benchmark solution, and calculating the unknown concentration ($C_s$) of the surfactant in the sample from the following equation: $C_s = C_{cm}/(C_{cm\ assumed}/C_{assumed})$.

Other aspects and advantages of this disclosure will be apparent from the following description made with reference to the accompanying drawings and the appended claims.

DETAILED DESCRIPTION

Embodiments disclosed herein relate generally to methods and apparatuses for determining an unknown surfactant concentration in a sample solution. The unknown surfactant concentration may be determined, for example, by using surface tension measurements from a single sample and a single benchmark solution. The surface tension measurements may then be used to determine a critical micelle concentration ("CMC") of the sample and benchmark solution. Other physical properties of a sample and comparative benchmark solution, such as conductivity or light absorption, may also be used to determine the CMC of the sample using methods and apparatuses disclosed herein.

As used herein, the CMC refers to the concentration of surfactants in a solution above which micelles or other surfactant aggregate form. When CMC is reached in a solution, additional surfactants added to the solution may also aggregate. Generally, the surface tension of a surfactant solution that has reached CMC may not change or may decrease at a notably reduced rate when additional surfactants are added to the solution. Accordingly, surface tension measurements of a solution containing surfactant may be used to determine a CMC of the surfactant. Using solution surface tension to determine a CMC of a surfactant may include taking surface tension measurements of the surfactant solution as the concentration of surfactant in the solution is changed and determining when the changes in surfactant concentration begin to have little or no effect on the surface tension of the surfactant solution.

For example, in some embodiments, a graph of surface tension measurements of a surfactant solution may be plotted against a change in surfactant concentration in the solution to determine the CMC of the surfactant. Surfactant concentration in a surfactant solution may be changed by adding a dilution fluid to the solution, where an increase in dilution fluid lowers the surfactant concentration in the solution, or by adding more of the surfactant to the solution, where an increase in the amount of the surfactant added to the solution increases the surfactant concentration in the solution.

Figure 1:
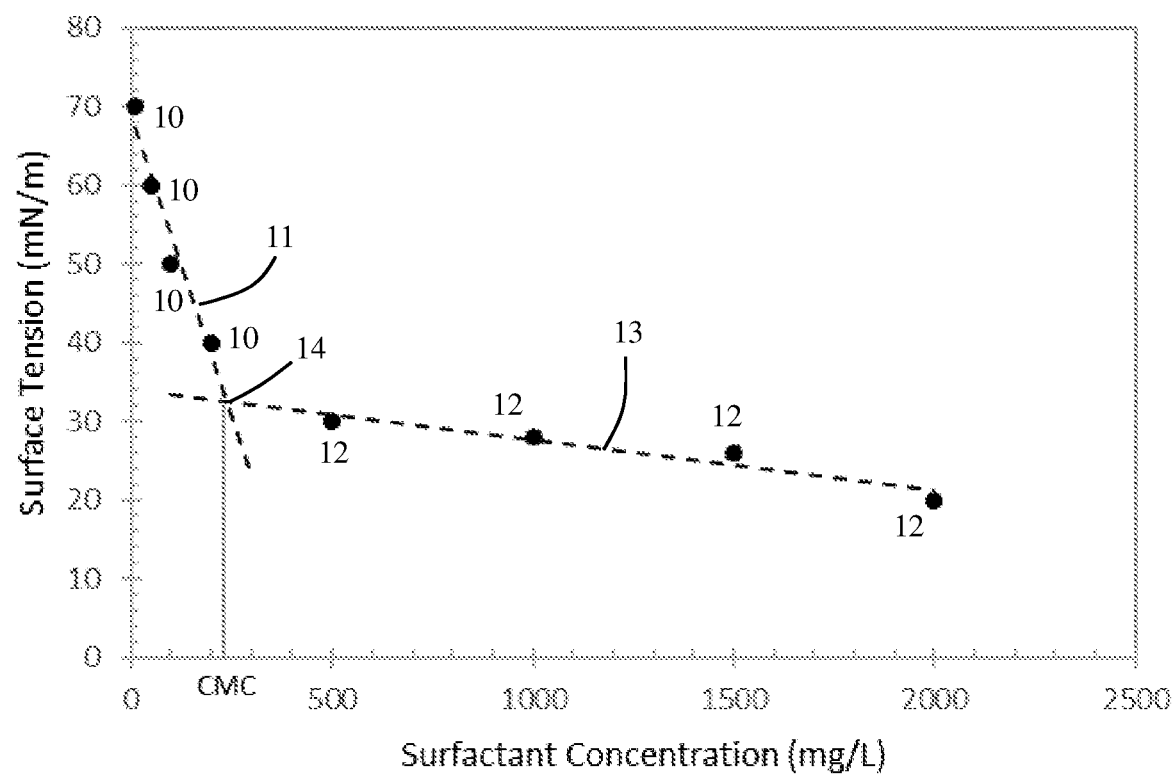
FIG. 1 shows a graph for determining a critical micelle concentration of a surfactant according to embodiments of the present disclosure.

FIG. 1 shows an example of a graph of the surface tension of a solution having a known type of surfactant as a function of the surfactant concentration of the solution. In the graph, data points 10, 12 of surface tensions measurements of the solution taken at different surfactant concentrations are plotted. The data points 10, 12 collected may be grouped into a first set of data points 10 and a second set of data points 12 based on their trending slope when a best-fit line, or trend line, is drawn between them. As shown, a first trend line 11 may be drawn among the first set of data points 10 showing a steeper change in surface tension measurements with respect to the change in surfactant concentration. A second trend line 13 may be drawn among the second set of data points 12 showing a relatively shallower change in surface tension measurements with respect to the change in surfactant concentration. The CMC of the surfactant may be identified at an intersection 14 between the first trend line 11 and the second trend line 13.

In some embodiments, surface tension measurements of a surfactant solution may be taken as the concentration of the surfactant in the solution is changed, where the surface tension measurements may be plotted on a graph as a function of the change in concentration and fitted with a single curved trend line. The CMC of the surfactant may be identified at the curved point in the trend line.

In some embodiments, an algorithm may be used to determine a change in slope or a change in trending surface tension from a plurality of surface tension measurements as the concentration of the surfactant in the solution is changed, where the change in slope or change in trend may be identified as the CMC point.

Methods disclosed herein may utilize the relationship between surface tension and surfactant concentration of a solution having a known type of surfactant therein to determine an unknown concentration of the surfactant in a sample solution.

In some methods, an unknown concentration of a surfactant in a sample may be determined using the relationship between surface tension and surfactant concentration, an assumed surfactant concentration assumption of the sample, and a benchmark solution having a known concentration of the surfactant therein. For example, FIG. 2 shows a block diagram of such methods.

Figure 2:
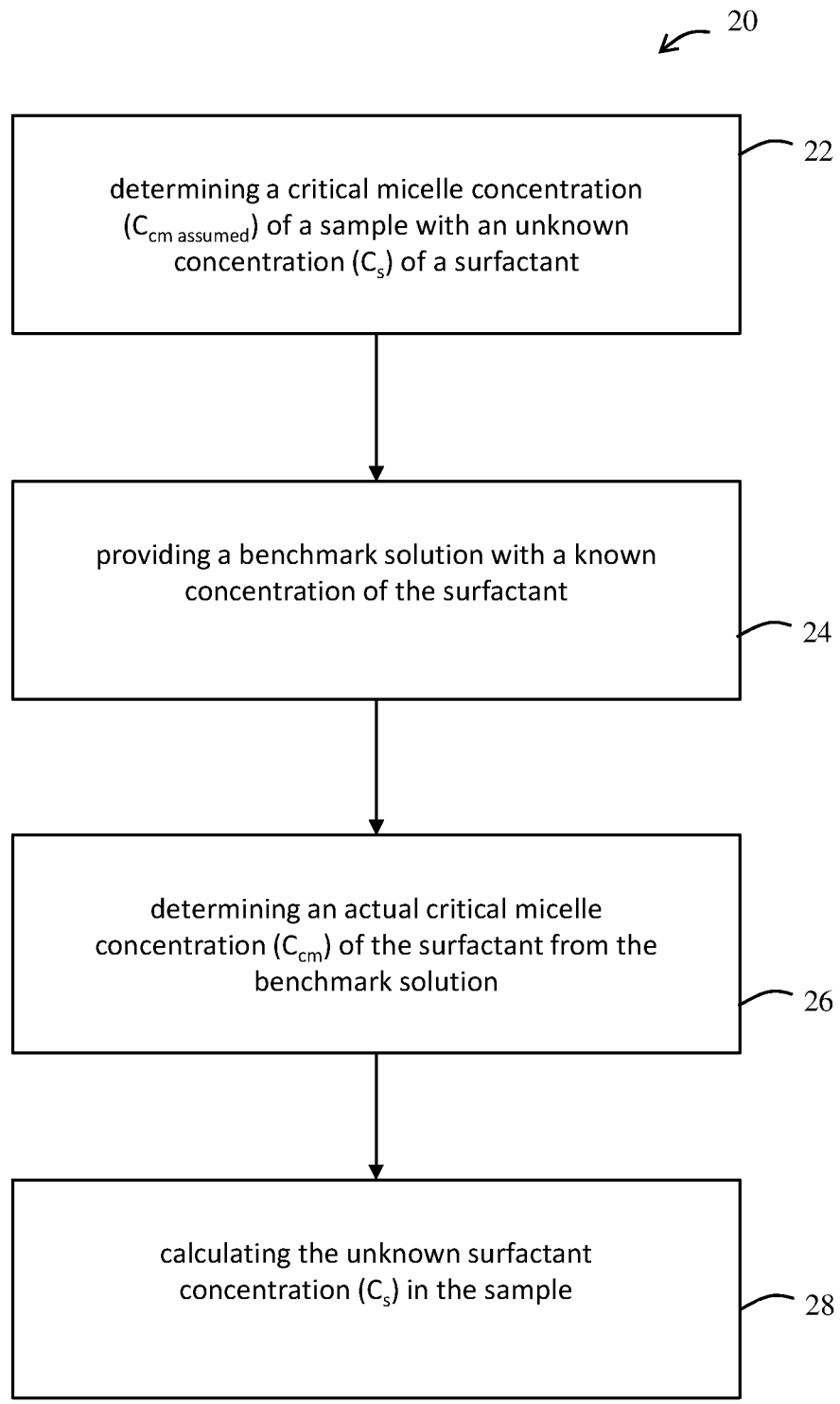
FIG. 2 shows a method according to embodiments of the present disclosure.

In the method 20 shown in FIG. 2, step 22 includes determining a critical micelle concentration ($C_{cm\ assumed}$) of a sample with an unknown concentration ($C_s$) of a known type of surfactant. The sample may include a base solution and the surfactant.

The CMC ($C_{cm\ assumed}$) of the sample with an unknown concentration ($C_s$) of the surfactant may be determined based on an assumed surfactant concentration ($C_{assumed}$) of the sample. For example, although selection of an assumed surfactant concentration in a sample may not be limited, a sample may be assumed to have, for example, between 5 and 50 percent by volume of a surfactant.

Further, the CMC ($C_{cm\ assumed}$) of the sample with the unknown concentration ($C_s$) of the surfactant may be determined by taking a plurality of surface tension measurements of the sample as the concentration of the surfactant in the sample is changed. For example, surface tension measurements of the sample may be taken (e.g., using a tensiometer) as the surfactant concentration in the sample is changed, which may be changed by adding a known amount of a dilution fluid to the sample to lower the surfactant concentration in the sample (dilute the sample), or by adding a known amount of the surfactant to the sample to increase surfactant concentration in the sample. The dilution fluid may have the same composition as the base fluid of the sample.

Surface tension measurements of the sample may be taken at regular or irregular dilution intervals. Further, surface tension measurements may be taken automatically or manually. For example, a tensiometer may be programmed to take surface tension measurements of a sample automatically at a regular interval and/or after each dilution interval of adding an amount of dilution fluid or adding an amount of surfactant.

The surface tension measurements of the sample may be plotted as a function of dilution, i.e., the change in surfactant concentration from the initially assumed surfactant concentration ($C_{assumed}$), in a graph of surface tension and surfactant concentration. Trend lines may be fitted among the data points, and the CMC ($C_{cm}$ assumed) of the sample may be determined from the graph at a point where the trend lines intersect, or at a point of a change in slope.

In some embodiments, the CMC ($C_{cm\ assumed}$) of the sample may be determined by taking a plurality of surface tension measurements of the sample as the surfactant concentration in the sample is changed, where the surface tension measurements may be plotted as a function of change in surfactant concentration on a graph and automatically analyzed by a computer algorithm to determine the CMC ($C_{cm\ assumed}$) of the sample (e.g., at an intersection between two fitted trend lines or a change in slope along a trend line) based on an initial assumed surfactant concentration ($C_{assumed}$) in the sample. Different computer algorithms may be used to analyze a plurality of surface tension measurements at different changes in surfactant concentration from an assumed surfactant concentration to interpolate a point at which the slope of the data points change, which may be identified as the CMC ($C_{cm\ assumed}$) of the of the sample.

The method 20 of FIG. 2 further shows step 24, which includes providing a benchmark solution with a known concentration of the surfactant. The benchmark solution may be made of the same base solution as the sample and the same type of surfactant as the sample. In step 26 of the method 20, an actual CMC ($C_{cm}$) of the surfactant may be determined from the benchmark solution. The actual CMC ($C_{cm}$) of the surfactant may be determined from the benchmark solution by taking a plurality of surface tension measurements of the benchmark solution as the surfactant concentration in the benchmark solution is changed, such as described above. The actual CMC ($C_{cm}$) of the surfactant may be determined from the benchmark solution using a different process or the same process for determining the critical micelle concentration ($C_{cm}$ assumed) in the sample.

For example, determining the actual CMC of a benchmark solution may include taking a plurality of surface tension measurements of the benchmark solution at dilution intervals, plotting the plurality of surface tension measurements as a function of dilution, and identifying the actual CMC at a change in slope along the plot. The dilution intervals may be provided, for example, by adding equal amounts of a dilution fluid or equal amounts of surfactant to the benchmark solution at a regular interval and/or after each surface tension measurement is taken. A dilution fluid may have the same composition as the base solution of the benchmark solution.

In step 28 of the method 20 shown in FIG. 2, the unknown surfactant concentration ($C_s$) in the sample may then be calculated from the initial assumed surfactant concentration ($C_{assumed}$) in the sample, the CMC ($C_{cm\ assumed}$) of the of the sample determined in step 22, and the actual CMC ($C_{cm}$) determined in step 26, using the following equation:

$$C_s = \frac{C^{cm}}{C^{cm}_{assumed}/C_{assumed}}.$$ Equation 1

In some embodiments, the method 20 may be used for solutions having a known mixture of surfactants (e.g., solutions with multiple co-surfactants), depending on the behavior of the base formulation and possibly for specific conditions. For example, in embodiments where the ratio of multiple surfactants in a sample is known and the known ratio is maintained when determining the actual CMC of a benchmark solution having the known ratio of multiple surfactants (i.e., a proportional reduction or consumption of the different surfactants in the formulation is expected without any chromatographic separation), the method 20 may be used to determine the unknown surfactant mixture concentration in the sample. In other words, where fractions of the components are roughly maintained, a benchmark solution having the proportional amounts of components may be prepared and used to determine an actual CMC, which may be used for calculating the unknown surfactant mixture concentration in a sample.

Figure 7:
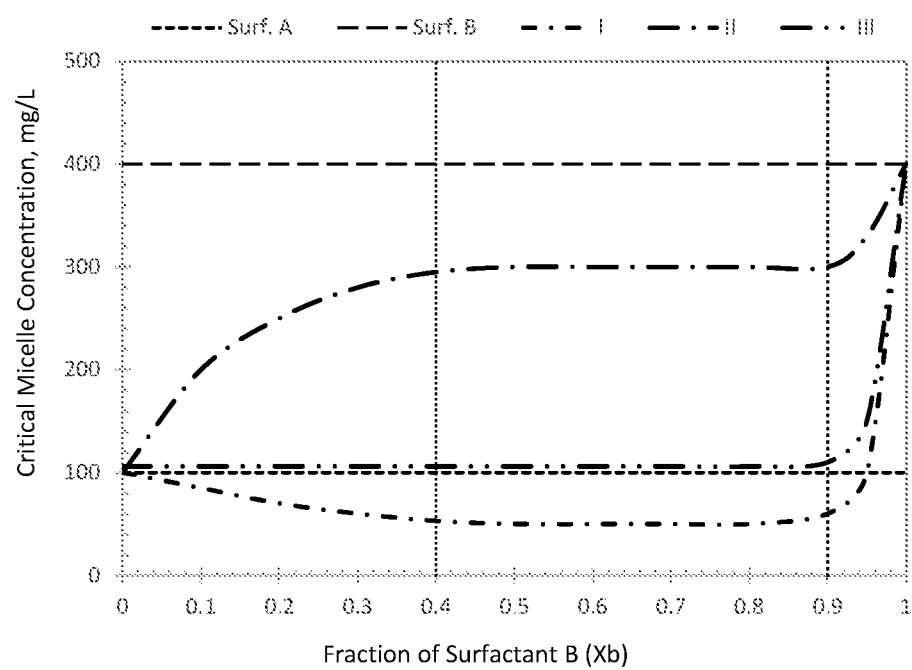
FIG. 7 shows a graph of the critical micelle concentration relationship with binary surfactant mixtures having different types of behaviors.

However, when the ratios of multiple surfactants may not be maintained during determining an actual CMC of a benchmark solution, the method for calculating an unknown surfactant mixture concentration in a sample may depend on the behavior of the surfactant mixture. For example, FIG. 7 shows a graphical representation of the relationship between CMC in varying ratios of a binary surfactant mixture under three types of behaviors. Under behavior type I, there is a synergy between the surfactants A and B that allows the mixture to form surfactant aggregates (micelles) and saturate the interface at a lower concentration. Under behavior type II, there is a negative effect where higher concentrations of the surfactants A and B can be accommodated at the interface. Under behavior type III, the interface is saturated by the most effective surfactant. The additional variable introduced for the binary mixtures is the ratio of surfactants (or fraction of a given surfactant, Xb). If Xb is known in priori, as explained above, and the known ratio may be maintained during testing, then a reference actual CMC may be determined, and a method 20 such as described with reference to FIG. 2 may be used to calculate an unknown surfactant concentration in a sample. If Xb is not known then the method 20 may be used when the binary surfactant mixture is known to follow the behavior type III, or when the binary surfactant mixture follows behavior types I or II but surfactant ratios are expected to be within the plateau window.

When using the methods 20 disclosed herein for mixtures of surfactants, the method 20 may be used to determine the total surfactant mixture concentration in a sample with the surfactant mixture, as opposed to the concentrations of the individual components of the surfactant mixture.

Further, the method 20 may be used with a solution having a surfactant forming an invert emulsion when a suitable sample can be collected. For example, when a sample of a representative surfactant solution (single-phase) can be collected from an emulsion, the sample may then be tested according to methods disclosed herein. Such representative sampling might be possible through selective extraction of aqueous phase with the assumptions that surfactants at interfaces represent a minute amount of the total concentration or by breakage of the emulsion through centrifugation or heating and subsequent sampling. In such manner, the CMC may be measured from solutions instead of emulsions (e.g. the CMC of a surfactant in a water solution that could form any sort of emulsion upon contact with an oleic phase).

Methods disclosed herein may be implemented on a computing system, which may be integrated with or separate from a measurement device according to embodiments disclosed herein. Any combination of mobile, desktop, server, router, switch, embedded device, or other types of hardware may be used.

Methods according to embodiments of the present disclosure have been tested and verified in the lab. One such test and the results are described with reference to FIG. 3, which shows a graph of surface tension measurements as a function of surfactant concentration. In the test, two samples having different concentrations of surfactants (1000 mg/L and 736 mg/L) were provided. The surfactant concentrations were unknown to the tester, but the type of surfactant used was known (e.g., the surfactant composition, manufacturer and/or code). A benchmark solution having the same type of surfactant at a surfactant concentration of 2000 mg/L was also provided. CMC measurements (derived from surface tension measurements taken as the surfactant concentration was changed) were performed using an automated ring-tensiometer assuming all three samples contained an initial surfactant concentration of 2000 mg/L. The obtained CMC results are summarized in Table 1, where the data for "Unknown 1" is for the first sample with an unknown surfactant concentration ($C_s$) and the data for "Unknown 2" is for the second sample with an unknown surfactant concentration ($C_s$).

TABLE 1

| Solution | Surfactant Concentration, mg/L | | Critical Micelle Concentration (CMC), mg/L | | |
|---|---|---|---|---|---|
| | Known | Assumed | High-estimate | Best-estimate | Low-estimate |
| Benchmark | 2000 | — | 1.330 | 1.222 | 1.069 |
| Unknown 1 | — | 2000 | 2.809* | 2.369* | 2.110* |
| Unknown 2 | — | 2000 | 3.973* | 3.135* | 2.839* |

Figure 3:
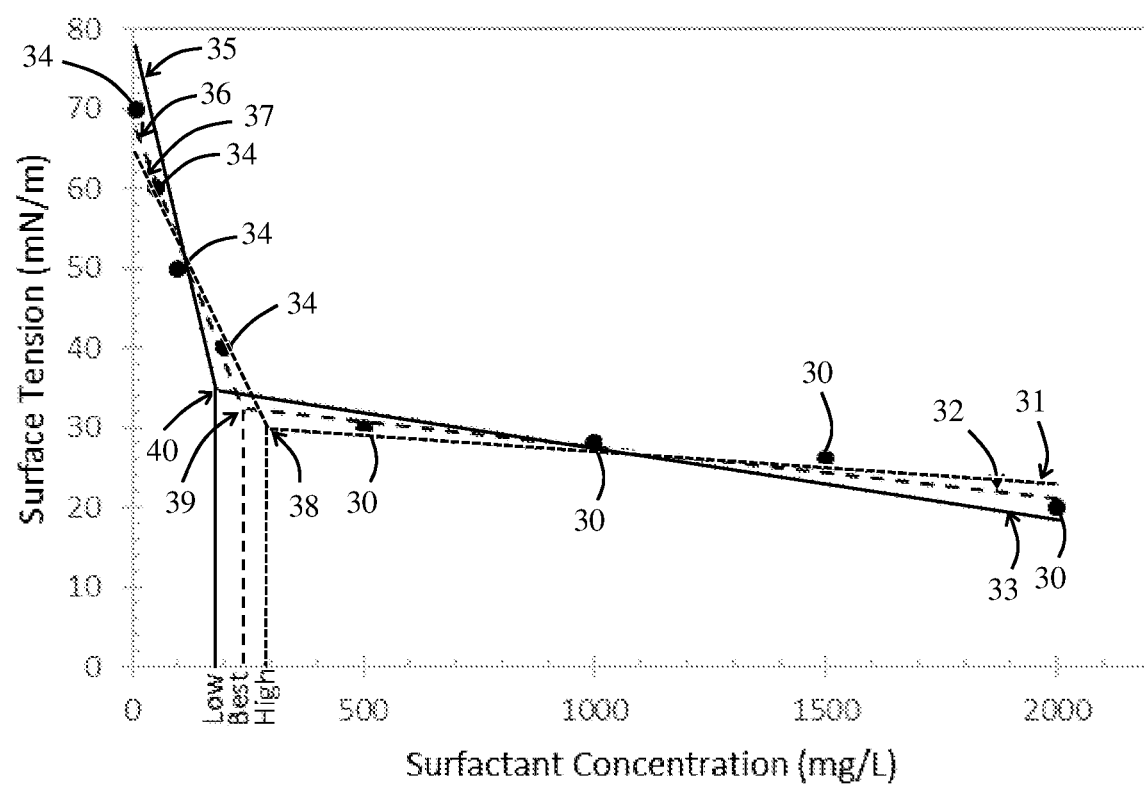
FIG. 3 shows a graph for determining a critical micelle concentration of a surfactant according to embodiments of the present disclosure.

The asterisked data in Table 1 indicate the values that are based on assumed surfactant concentrations ($C_{assumed}$) rather than actual, known surfactant concentrations. In addition, high-estimate, best-estimate, and low-estimate CMC values were determined from the CMC measurements. The high-estimate, best-estimate, and low-estimate CMC values were determined using three different possible trend lines drawn between the collected surface tension measurements, as depicted in FIG. 3. According to embodiments of the present disclosure, when surface tension measurements from a changing surfactant concentration do not have perfect or near perfect linearity (where a straight trend line may be drawn through a majority of the data points in a set of data points), more than one trend line may be drawn through the data points in a set of data points. For example, as shown in FIG. 3, three trend lines 31, 32, 33 may be drawn between the data points 30 in a first set of data points 30 representing post-CMC surface tension measurements in a sample, and three trend lines 35, 36, 37 may be drawn between the data points 34 in a second set of data points 34 representing pre-CMC surface tension measurements in the sample, where each trend line 31, 32, 33, 35, 36, 37 may be a possible best-fit through the data points 30, 34. The intersections 38, 39, 40 between the possible trend lines 31, 32, 33, 35, 36, 37 may represent a high-estimate, best-estimate, and low-estimate of the CMC value of a sample.

Using the best-estimate of the CMC measurements for the benchmark solution ($C_{cm}$), the first sample with unknown surfactant concentration ($C_{cm\ assumed}$), and the second sample with unknown surfactant concentration ($C_{cm\ assumed}$), the unknown surfactant concentrations ($C_s$) for the first and second samples were calculated using Equation 1:

$$C_s = \frac{C^{cm}}{C^{cm}_{assumed}/C_{assumed}}$$

For example, the unknown surfactant concentration ($C_s$) in the first sample may be calculated using Equation 1 and the best-estimate CMC value, where the known surfactant concentration ($C_{cm}$) in the benchmark solution is equal to 2,000 mg/L, the best-estimate CMC value ($C_{cm\ assumed}$) for the first sample is 2.369 mg/L (shown in Table 1), the assumed surfactant concentration ($C_{assumed}$) in the first sample is 2,000 mg/L, and the unknown surfactant concentration ($C_s$) in the first sample is calculated as 1,032 mg/L. The unknown surfactant concentration ($C_s$) in the first sample based on the high and low CMC estimates and the unknown surfactant concentration in the second sample based on the different CMC estimates may similarly be calculated from Equation 1. The results are shown in Table 2, below, along with some measures of accuracy, which are within acceptable limits for many applications.

TABLE 2

| Solution | Calculated Surfactant Concentration, mg/L | | | Accuracy Measures | |
|---|---|---|---|---|---|
| | Low-estimate | Best-estimate | High-estimate | Potential Uncertainty, ± % | Actual Error, % |
| Unknown 1 | 870.1 | 1032 | 1158 | 13.97 | 3.166 |
| Unknown 2 | 615.2 | 779.6 | 860.9 | 15.76 | 5.922 |

Other methods may similarly use different physical properties (e.g., conductivity or absorption) of a solution to calculate an unknown surfactant concentration in a sample. For example, a measurement device such as a spectrometer or electrical conductivity meter may be used to take physical property measurements other than surface tension measurements of a sample and corresponding benchmark solution at different dilution intervals to calculate an unknown surfactant concentration in the sample using the comparative methods disclosed herein. Thus, while description of methods using surface tension measurements is described herein, methods may similarly use other physical property measurements of a sample and corresponding benchmark solution for calculating an unknown surfactant concentration in the sample.

For example, according to some embodiments, a measurement device may take a plurality of physical property measurements (e.g., surface tension measurements, ultraviolet absorption measurements, conductivity measurements, nuclear magnetic resonance (NMR) chemical shifts, or fluorescence) of a sample with an unknown concentration ($C_s$) of a surfactant and of a benchmark solution with a known concentration of the surfactant. An assumed critical micelle concentration ($C_{cm\ assumed}$) of the sample may be determined from the plurality of physical property measurements of the sample and based on an assumed surfactant concentration ($C_{assumed}$) of the sample. An actual critical micelle concentration ($C_{cm}$) of the surfactant in the benchmark solution may be determined from the plurality of physical property measurements of the benchmark solution. The unknown concentration ($C_s$) of the surfactant in the sample may then be calculated from the following equation: $C_s = C_{cm}/(C_{cm\ assumed}/C_{assumed})$.

According to embodiments of the present disclosure, determining the CMC ($C_{cm}$ assumed) of a sample and determining the actual CMC ($C_{cm}$) of a corresponding benchmark solution (where the sample and the benchmark solution may have a base solution with substantially the same composition and the same type of surfactant) may include simultaneously taking a plurality of physical property measurements, such as surface tension measurements, of the sample and the benchmark solution. For example, surface tension measurements of the sample and corresponding benchmark solution may be taken concurrently using measurement devices according to embodiments disclosed herein, where the sample and benchmark solution may be provided in separate fluid chambers accessible to different tensiometers, and where the tensiometer for each fluid chamber may concurrently take the surface tension measurements. In such embodiments, the surfactant concentrations of the sample and benchmark solution may also be changed concurrently (e.g., by adding an amount of dilution fluid or by adding an amount of surfactant) and/or be changed by adding the same amount of dilution fluid or surfactant. An amount of dilution fluid or an amount of surfactant may be added to each of the sample and the benchmark solution after each surface tension measurement is taken.

Measurement devices according to embodiments of the present disclosure may include a sample chamber, which may be used to hold a sample solution, a benchmark chamber, which may be used to hold a benchmark solution, at least one tensiometer, and a housing containing the sample chamber, the benchmark chamber, and the tensiometer(s). Measurement devices according to embodiments of the present disclosure may include various types of tensiometers capable of taking surface tension measurements of a fluid, such as a ring tensiometer, a plate tensiometer, a bubble pressure tensiometer, and/or a tensiometer that calculates surface tension from drop profiles. In embodiments using physical property measurements other than surface tension to calculate an unknown surfactant concentration, measurement devices other than a tensiometer may be provided, such as an ultraviolet spectrometer, a NMR spectrometer, a fluorescence spectrometer, or an electrical conductivity meter.

Figure 4:
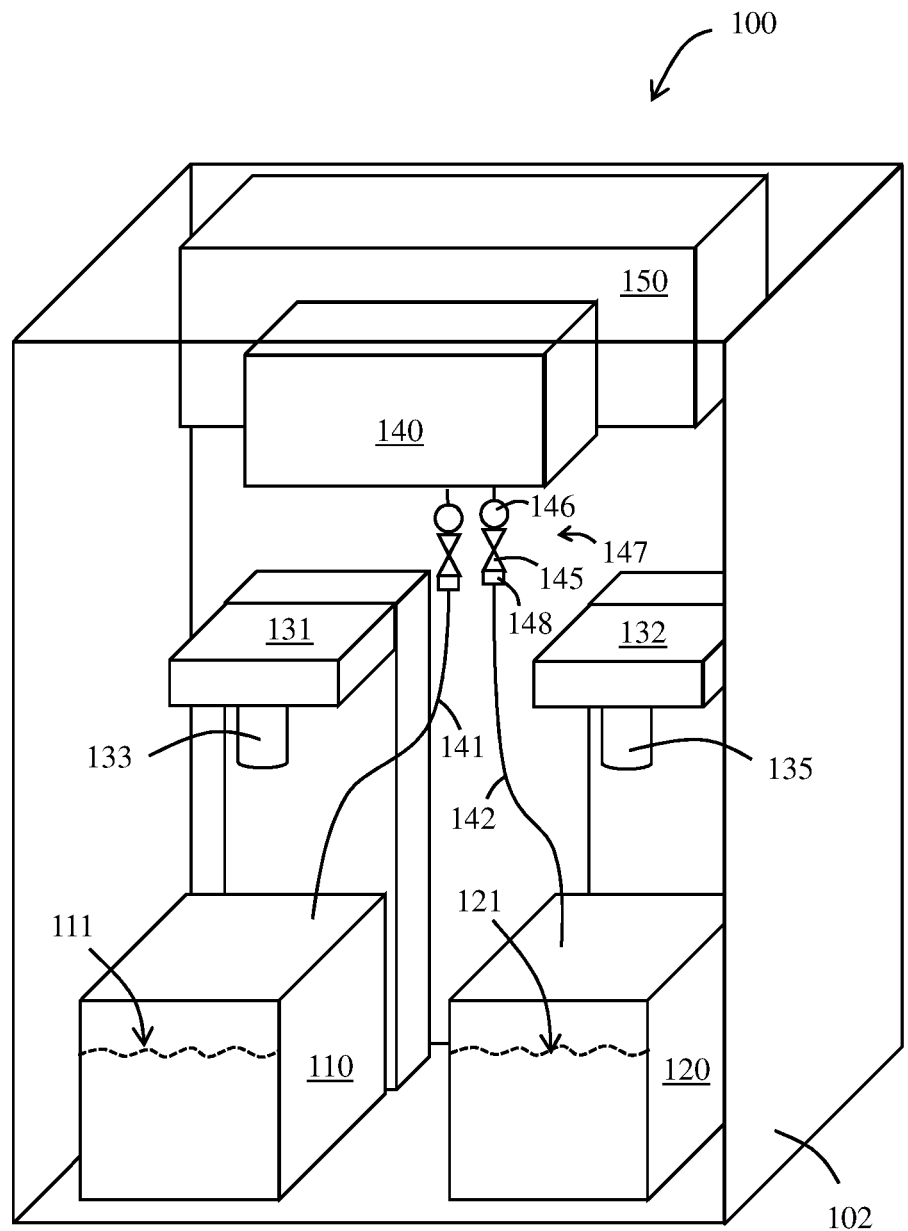
FIG. 4 shows a measurement device according to embodiments of the present disclosure.

FIG. 4 shows a schematic of an example measurement device 100 according to embodiments of the present disclosure. The device 100 includes a sample chamber 110 holding a sample solution 111, a benchmark chamber 120 holding a benchmark solution 121, a first tensiometer 131 adjacent to the sample chamber 110, a second tensiometer 132 adjacent to the benchmark chamber 120, a concentration fluid chamber 140 (which may contain a concentration fluid of dilution fluid or additional surfactant) in fluid communication with the sample chamber 110 and benchmark chamber 120, and a computing system 150. The embodiment in FIG. 4 shows components that are optional in the design of a measurement device according to embodiments of the preset disclosure but are shown to provide a reference in their more detailed description below. Other embodiments of measurement devices may exclude one or more of the components shown in FIG. 4. For example, in some embodiments, a measurement device may include a tensiometer, a concentration fluid chamber, and a computing system, while the sample solution and benchmark solution may be provided separately from the measurement device. In some embodiments, a measurement device may include a tensiometer and a computing system, while the sample solution, benchmark solution, and concentration fluid (a dilution fluid or additional surfactant) may be provided separately from the measurement device.

A housing 102 may contain the components of the device 100, including the sample chamber 110, the benchmark chamber 120, the tensiometers 131, 132, the concentration fluid chamber 140, the computing system 150, and lines of fluid and/or electrical communication therebetween. The geometry of the housing 102 may be altered depending on, for example, the shapes, sizes, and arrangement of the components therein. Further, the housing 102 may fully enclose the components therein, such as shown in FIG. 4, where the components therein may be accessible through one or more closable openings. In other embodiments, a housing of a measurement device may partially (not entirely) enclose the components therein. For example, a measurement device may have a housing that contains one or more tensiometers, a concentration fluid chamber, and a computing system, while the sample(s) and benchmark solution may be provided for testing outside the measurement device.

The first and second tensiometers 131, 132 may be the same type or different type of tensiometer, while both are capable of measuring the surface tension of the solutions in adjacent chambers. The first tensiometer 131 may be positioned next to the sample chamber 110 such that a measuring probe 133 (e.g., a ring of a ring tensiometer or a plate of a plate tensiometer) may access the sample solution 111 in the sample chamber 110 to take surface tension measurements of the sample solution 111. Similarly, the second tensiometer 132 may be positioned next to the benchmark chamber 120 such that a measuring probe 135 may access the benchmark solution 121 in the benchmark chamber 120 to take surface tension measurements of the benchmark solution 121. In the embodiment shown, two tensiometers are shown in the measurement device 100. By providing a tensiometer 131, 132 for each fluid to be tested (e.g., sample solution 111 and benchmark solution 121), the fluids may be measured concurrently. However, in other embodiments, one tensiometer may be provided in a measurement device that is positioned to move (e.g., through motorized movement) to multiple fluid chambers in the device to take surface tension measurements of solutions within each fluid chamber.

While tensiometers 131, 132 are described with reference to the device 100 in FIG. 4, other measurement devices for measuring a physical property of a solution may be provided in the housing 102. Other measurement devices may include but are not limited to electrical conductivity meters and different types of spectrometers.

Further, in some embodiments, more than one sample chamber may be provided within a measurement device. For example, a measurement device may include a benchmark chamber and two or more sample chambers, where one or more tensiometers may be positioned to take surface measurements of solutions within the benchmark and sample chambers. In such embodiments, multiple sample solutions may be tested using the benchmark solution in the benchmark chamber.

The device 100 may also include a concentration fluid chamber 140 in fluid communication with the sample chamber 110 and the benchmark chamber 120. The concentration fluid chamber 140 may hold a fluid for changing the concentration of a sample and/or benchmark solution, such as a dilution fluid (which may have the same composition as a base solution of the sample and/or benchmark solution) or a surfactant (which may be the same type of surfactant in the sample and benchmark solution). As shown in the embodiment of FIG. 4, a flow path 141 may extend between the concentration fluid chamber 140 and the sample chamber 110, and a second flow path 142 may extend between the concentration fluid chamber 140 and the benchmark chamber 120. Fluid used to change the surfactant concentration in the sample solution 111 and the benchmark solution 121 as surface tension measurements are taken may flow from the concentration fluid chamber 140 and into the sample chamber 110 and/or benchmark chamber 120 through the respective flow paths 141, 142 extending therebetween.

In some embodiments, a measurement device may not include a concentration fluid chamber. In such embodiments, fluid used to change the surfactant concentration for CMC testing (e.g., dilution fluid or surfactant) may be added to a sample chamber and/or a benchmark chamber from a source outside the measurement device. In some embodiments, more than one concentration fluid chamber may be provided within a measurement device housing. For example, a measurement device may contain a first concentration fluid chamber holding a dilution fluid and a second concentration fluid chamber holding a surfactant. Measurement devices containing both a dilution fluid source and a surfactant source may both increase and decrease the surfactant concentration in a sample and/or benchmark solution.

A measurement device 100 according to embodiments of the preset disclosure may further include at least one valve 145 (e.g., ball valve, gate valve, or other type valve) positioned along a flow path 141, 142 between the concentration fluid chamber 140 and the sample and benchmark chambers 110, 120. The valve 145 may be manually operated or automatically actuated to an open position (to allow fluid flow through the flow path 141, 142) and a closed position (to prevent fluid flow through the flow path 141, 142).

For example, in some embodiments, an automatic dilution mechanism 147 having at least one valve 145 and at least one flow meter 146 may be provided along the flow path 141, 142. The automatic dilution mechanism 147 may be programmed to maintain the valve 145 in a closed position and open the valve 145 at select times for a duration to allow a select amount of fluid (dilution fluid or a surfactant) from the concentration fluid chamber 140 to flow into the sample chamber 110 and/or benchmark chamber 120. A select amount of fluid may be passed through the automatic dilution mechanism 147, for example, by measuring the flow of the fluid through the flow path 141, 142 with a flow meter 146, and when the pre-selected amount of fluid has passed through the automatic dilution mechanism 147, the valve 145 may be closed.

A valve 145 in the measurement device 100 may be opened/closed by a valve position controller 148 connected to the valve and in communication with a computer processor (e.g., provided in computing system 150). The computer processor may execute programmed instructions (e.g., instructions stored in a non-transitory computer readable medium) to open the valve 145 to allow an amount of a concentration fluid (e.g., dilution fluid or additional surfactant) to flow into the sample chamber, opening the valve 145 to allow a second amount of the concentration fluid to flow into the benchmark chamber, and closing the valves.

Measurement devices 100 according to embodiments of the preset disclosure may include a computing system 150 that includes a computer processor and at least one input device connected to the computer processor. A non-transitory computer readable medium storing instructions executable by the computer processor may be provided, where the instructions comprise functionality for performing one or more methods according to embodiments of the present disclosure. For example, programmed instructions may include 1) obtaining from the tensiometer(s) a plurality of surface tension measurements of a sample 111 with an unknown surfactant concentration ($C_s$) in the sample chamber 110 and of a benchmark solution 121 with a known surfactant concentration in the benchmark chamber 120; 2) determining a critical micelle concentration ($C_{cm\ assumed}$) of the sample 111 from the plurality of surface tension measurements of the sample 111 and based on an assumed surfactant concentration ($C_{assumed}$) of the sample; 3) determining an actual critical micelle concentration ($C_{cm}$) of the surfactant in the benchmark solution 121 from the plurality of surface tension measurements of the benchmark solution 121; and 4) calculating the unknown concentration ($C_s$) of the surfactant in the sample from Equation 1 (also provided above), $C_s = C_{cm}/(C_{cm\ assumed}/C_{assumed})$. Instructions may also include direction as to how and when the surfactant concentration in the sample chamber 110 and benchmark chamber 120 is changed while taking surface tension measurements, for example, when to open and close valves allowing concentration fluid to flow from the concentration fluid chamber 140 into the sample and/or benchmark chambers 110, 120, such as described above.

In some embodiments, programmed instructions may include 1) obtaining from one or more measurement devices other than a tensiometer (e.g., a spectrometer or electrical conductivity meter) a plurality of physical property measurements of a sample 111 with an unknown surfactant concentration ($C_s$) in the sample chamber 110 and of a benchmark solution 121 with a known surfactant concentration in the benchmark chamber 120; 2) determining a critical micelle concentration ($C_{cm\ assumed}$) of the sample 111 from the plurality of physical property measurements of the sample 111 and based on an assumed surfactant concentration ($C_{assumed}$) of the sample; 3) determining an actual critical micelle concentration ($C_{cm}$) of the surfactant in the benchmark solution 121 from the plurality of physical property measurements of the benchmark solution 121; and 4) calculating the unknown concentration ($C_s$) of the surfactant in the sample from Equation 1 (also provided above), $C_s = C_{cm}/(C_{cm\ assumed}/C_{assumed})$.

The housing 102 of the measurement device 100 may contain and hold in place components within the measurement device 100 (e.g., using fasteners, integrally forming the housing with one or more fluid chambers, using adhesives, welding, using brackets, etc.), such that the measurement device 100 may be portable. Portable measurement devices according to embodiments of the preset disclosure may have sealable fluid chambers (e.g., the sample chamber 110, the benchmark chamber 120, and the concentration fluid chamber 140), where a fluid chamber may be opened to access, deposit or withdraw fluids from therein and sealingly closed to contain the fluids from spilling (such as when the device is being moved).

In some embodiments, a portable measurement device may be a tensiometer or other measurement device (e.g., electrical conductivity meter) having a computing system integrated therewith. In such embodiments, the measurement device may be positioned adjacent to sample(s) and a benchmark solution provided separately from the measurement device, where surfactant concentrations in the sample(s) and benchmark solution may be changed using a concentration fluid (dilution fluid or additional surfactant) provided separately from the measurement device.

According to embodiments of the present disclosure, portable measurement devices may be limited in size and weight. For example, a portable measurement device may weigh less than 40 pounds, less than 20 pounds, less than 15 pounds, or less than 10 pounds, and/or have a size less than 6 cubic feet, less than 4 cubic feet, or less than 1 cubic feet.

Figure 5:
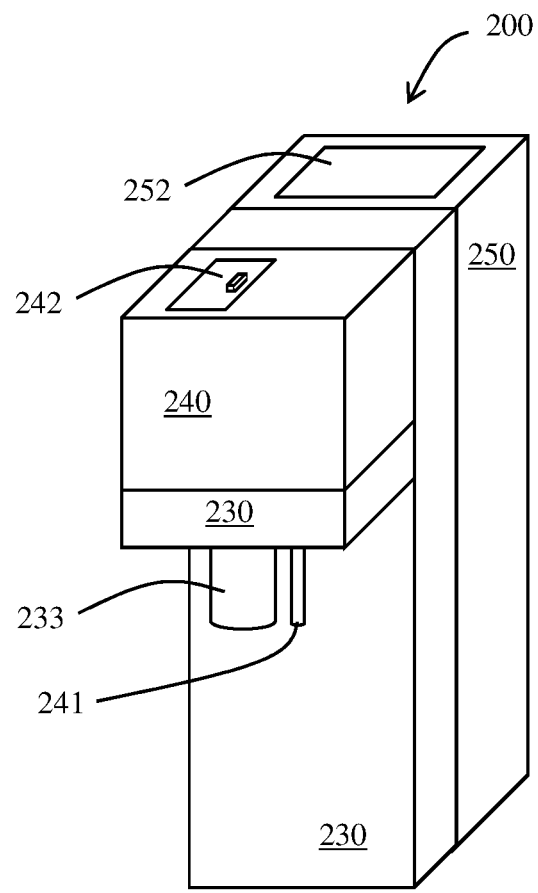
FIG. 5 shows a measurement device according to embodiments of the present disclosure.
Figure 5:
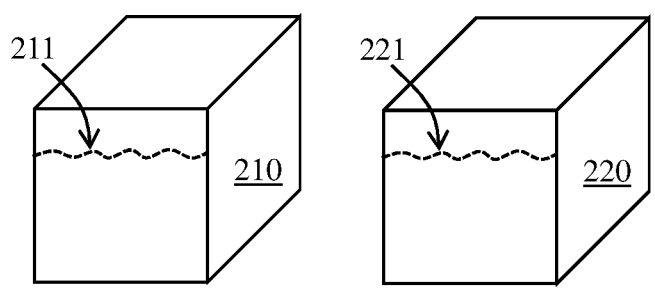

FIG. 5 shows a schematic of an example portable measurement device 200 according to embodiments of the present disclosure that includes a tensiometer 230, a concentration fluid chamber 240, and a computing system 250. The computing system 250 may be integrated into the tensiometer housing or may be separately compartmentalized and in communication with the tensiometer 230. The tensiometer 230 may include a measuring probe 233, e.g., a ring of a ring tensiometer, a plate of a plate tensiometer, a capillary tube for a gas stream in a bubble tensiometer, etc., which may be inserted into a fluid for surface tension measurements. The concentration fluid chamber 240 may have a flow path 241 extending out of the concentration fluid chamber 240 to provide an outlet through which concentration fluid may flow into a sample and/or benchmark solution for changing the surfactant concentration of the sample and/or benchmark solution during surface tension measurements. In the embodiment shown, the flow path 241 from the concentration fluid chamber 240 may extend through a portion of the tensiometer 230 and near the measuring probe 233 of the tensiometer 230. Other embodiments may have different configurations of the concentration fluid chamber 240 and/or flow path 241 to allow concentration fluid to be delivered to a sample and/or benchmark solution. The concentration fluid chamber 240 may further include an access point 242, which may be, for example, a door, a cap, or a closable lid. A concentration fluid may be poured into the concentration fluid chamber 240 or emptied from the concentration fluid chamber 240 via the access point 242.

The measurement device 200 may have one or more sample solution 211 and a benchmark solution 221 provided separately from the device 200, for example, in a separate sample chamber 210 and a separate benchmark chamber 220. The sample 211 and the benchmark solution 221 may be sequentially positioned adjacent the tensiometer 230 portion of the device for surface tension measurements and CMC determinations. For example, the sample 211 may first be positioned adjacent the tensiometer 230 portion of the device 200 for the tensiometer to take surface tension measurements of the sample 211 as the surfactant concentration in the sample is changed with addition of concentration fluid from the concentration fluid chamber 240 and to determine the CMC of the sample based on an initially assumed surfactant concentration. The sample 211 may then be removed, and the benchmark solution 221 may be positioned adjacent the tensiometer 230 portion of the device 200 for the tensiometer to take surface tension measurements of the benchmark solution 221 as the surfactant concentration in the benchmark solution is changed with addition of concentration fluid from the concentration fluid chamber 240 and to determine the CMC of the benchmark solution 221. Alternatively, surface tension measurements and CMC determination of the benchmark solution 221 may be performed before the sample 211.

The computing system 250 may include one or more computer processors, one or more storage elements, a communication interface, and other elements useful in computing. Software instructions in the form of computer readable program code to perform embodiments of the present disclosure may be stored, in whole or in part, temporarily or permanently, on a non-transitory computer readable medium such as a CD, DVD, storage device, a diskette, a tape, flash memory, physical memory, or any other computer readable storage medium, which may be executed by the computing system 250. Specifically, the software instructions may correspond to computer readable program code that when executed by a processor(s) in the computing system 250, is configured to perform embodiments disclosed herein.

For example, the computing system 250 may include a non-transitory computer readable medium storing instructions executable by a computer processor that may direct the tensiometer to take a plurality of surface tension measurements, direct a change in surfactant concentration, calculate CMC, process one or more inputs and/or produce one or more outputs.

The computing system 250 may further include a user interface 252, which may include a graphical user interface (GUI) that displays information on a display device (e.g., screen or touchscreen) and/or may include one or more buttons (e.g., a numerical key pad, an alphanumeric key pad, or keyboard). Through the user interface, a user may input test parameters, retrieve data, etc. In some embodiments, data may be retrieved from and/or inputted into the computing system 250 through one or more connections to the computing system 250 by an external computing system.

Figure 6:
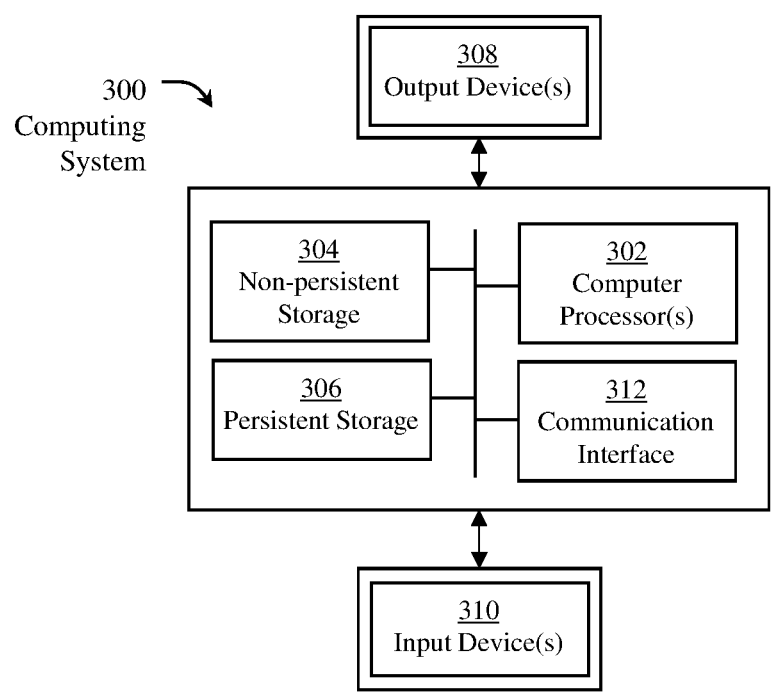
FIG. 6 shows a schematic diagram of a computing system according to embodiments of the present disclosure.

FIG. 6 shows a schematic diagram of a computing system 300 that may be used with embodiments of the present disclosure. The computing system 300 may include one or more computer processors 302, non-persistent storage 304 (e.g., volatile memory, such as random access memory (RAM), cache memory), persistent storage 306 (e.g., a hard disk, an optical drive such as a compact disk (CD) drive or digital versatile disk (DVD) drive, a flash memory, etc.), a communication interface 312 (e.g., Bluetooth interface, infrared interface, network interface, optical interface, etc.), and numerous other elements and functionalities.

The computer processor(s) 302 may be an integrated circuit for processing instructions. For example, the computer processor(s) may be one or more cores or micro-cores of a processor. The computing system 300 may also include one or more input devices 310, such as a touchscreen, keyboard, mouse, microphone, touchpad, electronic pen, or any other type of input device.

The communication interface 312 may include an integrated circuit for connecting the computing system 300 to a network (not shown) (e.g., a local area network (LAN), a wide area network (WAN) such as the Internet, mobile network, or any other type of network) and/or to another device, such as another computing device.

Further, the computing system 300 may include one or more output devices 308, such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) 302, non-persistent storage 304, and persistent storage 306. Many different types of computing systems exist, and the aforementioned input and output device(s) may take other forms.

The computing system or group of computing systems described in FIG. 6 may include functionality to perform a variety of operations disclosed herein. For example, the computing system(s) may perform communication between processes on the same or different systems (e.g., communication between one or more valves to open/close the valve, communication with a tensiometer to perform one or more function such as moving the tensiometer and taking a surface tension measurement and process data received from the tensiometer). A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

The computing system performing one or more embodiments of the disclosure may include functionality to receive data from a user. For example, in one or more embodiments, a user may submit data via a GUI on the user device. Data may be submitted via the GUI by a user selecting one or more GUI widgets or inserting text and other data into GUI widgets using a touchpad, a keyboard, a mouse, or any other input device. For example, data inputted by a user via a GUI may include but is not limited to an assumed surfactant concentration, selection of a type of surfactant being analyzed, selection of a fluid type (e.g., sample or benchmark solution) being analyzed, type of display for calculated results (e.g., data displayed as a chart or graph), the amount of surface tension measurements to take, and intervals of change in surfactant concentration (e.g., dilution intervals and/or amount of additional surfactant added before each surface tension measurement). In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data, e.g., CMC values determined from multiple trend lines through surface tension measurements.

The extracted data may be used for further processing by the computing system. For example, the computing system of FIG. 6, while performing one or more embodiments of the disclosure, may perform data comparison. Data comparison may be used to compare two or more data values (e.g., surface tension measurements and CMC values). For example, one or more embodiments may determine a slope between surface tension measurements, or if a change in slope between surface tension measurements that is greater than, equal to or less than a selected value, etc. The comparison may be performed by submitting data values, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, where A and B may represent data from methods of the present disclosure such as surface tension measurements, surfactant concentration values, CMC values, etc., B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments, if A and B are strings, the binary values of the strings may be compared.

The computing system in FIG. 6 may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 6 may include functionality to present raw and/or processed data, such as results of comparisons and other processing. For example, presenting data may be accomplished through various presenting methods. Specifically, data may be presented through a user interface provided by a computing device or by a measurement device of the present disclosure. The user interface may include a GUI that displays information on a display device, such as a display device on a measurement device disclosed herein, a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing system into a visual representation of the data, such as through visualizing a data model.

For example, a GUI may first obtain a notification from a software application requesting that a particular data object (e.g., CMC value or other data from methods of the present disclosure) be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

The above description of functions presents only a few examples of functions performed by the computing system of FIG. 6. Other functions may be performed using one or more embodiments of the disclosure.

In some embodiments, a measurement device may include a computing system having software instructions for obtaining a plurality of surface tension measurements of a sample with an unknown surfactant concentration ($C_s$) and of a benchmark solution with a known surfactant concentration from a tensiometer. Such instructions may include, for example, instructions for at least one of lowering a measuring probe of the tensiometer into a solution, generating a control signal for the tensiometer to change the surfactant concentration of the sample and the benchmark solution when taking the plurality of surface tension measurements of the sample and of the benchmark solution, for example, diluting a solution (e.g., at a regular or irregular interval, adding a selected amount of dilution fluid, opening and/or closing a valve to allow dilution fluid to flow into a solution, etc) or adding an amount of surfactant to a solution, and storing collected surface tension measurements in a memory of the computing system.

Instructions executable by the computing system may also include instructions to determine a critical micelle concentration ($C_{cm\ assumed}$) of the sample from the plurality of surface tension measurements of the sample and based on an assumed surfactant concentration ($C_{assumed}$) of the sample. Such instructions may include, for example, instructions to plot the surface tension measurements as a function of the surfactant concentration of the sample, to generate best-fit or trend lines among the plotted surface tension measurements, calculating a slope between collected surface tension measurements, determining a change in slope between the collected surface tension measurements, and/or determining an intersection point between two trend lines drawn among the collected surface tension measurements.

Instructions executable by the computing system may also include instructions to determine an actual critical micelle concentration ($C_{cm}$) of the surfactant in the benchmark solution from the plurality of surface tension measurements of the benchmark solution. Such instructions may include, for example, instructions to plot the surface tension measurements as a function of the surfactant concentration of the benchmark solution, to generate best-fit or trend lines among the plotted surface tension measurements, calculating a slope between collected surface tension measurements, determining a change in slope between the collected surface tension measurements, and/or determining an intersection point between two trend lines drawn among the collected surface tension measurements.

Instructions executable by the computing system may also include instructions to calculate the unknown concentration ($C_s$) of the surfactant in the sample from the Equation 1: $C_s = C_m / (C_{cm\ assumed} / C_{assumed})$.

Data inputted for processing by the instructions and/or data generated from execution of one or more instructions may be inputted by and/or retrieved through at least one input device connected to the computer processor. Accordingly, instructions executable by the computing system may further include functionality for receiving a control signal from the at least one input device.

Advantageously, embodiments of the present disclosure may utilize a simplified process for determining an unknown surfactant concentration in a sample that includes comparison between a CMC value of the sample based on an assumed surfactant concentration and an actual CMC value of a single benchmark solution. Methods according to embodiments of the present disclosure may be programmed into a measurement device, which may incorporate one or more tensiometers to perform one or more steps of the methods.

Further, by using the methods according to embodiments of the preset disclosure, a measurement device incorporating such methods may be made to be portable and transportable. For example, a measurement device according to embodiments of the present disclosure may be handheld-size.

Methods disclosed herein may be used for various types of fluid solutions and applications in different industries. For example, a solution containing surfactant may include but is not limited to water, detergents, fabric softeners, pharmaceuticals, biosurfactant solutions, emulsion solutions, paints, adhesives, agricultural solutions such as insecticides, soaps, cosmetics, inks, anti-fogs, and solutions used in hydrocarbon recovery operations such as drilling fluids, treatment fluids, fracturing fluids, etc.

In some embodiments, an unknown concentration of a surfactant in well or drilling effluent may be determined using methods and/or apparatuses disclosed herein. For example, in hydrocarbon recovery applications, surfactants may be used in drilling fluid and/or fracturing fluid, which may be adsorbed onto rock surfaces or otherwise lost during operation. By determining the concentration of surfactant remaining in the effluent (when the drilling and/or fracturing fluid returns to the surface), the amount of surfactant lost during the recovery or drilling operation may be estimated. The amount of surfactant lost may be used to estimate how much of the surfactant was adsorbed by the rock formation in the hydrocarbon recovery operation, which may then be used to help determine adsorption characteristics of the formation.

Further, the type of surfactant being measured using methods and apparatuses of the present disclosure may include, but is not limited to biosurfactants, fluorosurfactants, siloxane surfactants, zwitterionic surfactants such as phosphatidylserine, phosphatidylethanolamine, phosphatidylcholine, and sphingomyelins, anionic surfactants such as those having sulfates, sulfonates, phosphates, and carboxylates, docusate, perfluorooctanessulfonate (PFOS), perfluorobutanesulfonate, alkyl-aryl ether phosphates, alkyl ether phosphates, carboxylates such as carboxylate salts, sodium stearate, and sodium lauroyl sarcosinate, carboxylate-based fluorosurfactants such as perfluorononanoate (PFOA) and perfluorooctanoate (PFO), cationic surfactants such as octenidine dihydrochloride, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), and other quaternary ammonium surfactants, and non-ionic surfactants such as ethoxylates, fatty alcohol ethoxylates (e.g., narrow-range ethoxylate, octaethylene glycol monododecyl ether, and entaethylene glycol monododecyl ether), alkylphenol ethoxylates (APEs) (e.g., nonoxynols), fatty acid ethoxylates, ethoxylated amines and/or fatty acid amides (e.g., polyethoxylated tallow amine, cocamide monoethanolamine, and cocamide diethanolamine), poloxamers, glycerol monostearate, glycerol monolaurate, fatty acid esters of sorbitol (e.g., sorbitan monolaurate, sorbitan monostearate, sorbitan tristearate), polysorbates, fatty acid esters of sucrose, alkyl polyglucosides (e.g., decyl glucoside, lauryl glucoside, and octyl glucoside), lauryldimethylamine oxide and other amine oxides, dimethyl sulfoxide, and phosphine oxide. Methods and apparatuses disclosed herein are also applicable to determining the concentration of other types of surfactants not explicitly recited above.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A device, comprising:
    a measurement device for measuring a physical property of a solution, the measurement device selected from a tensiometer, a spectrometer, and an electrical conductivity meter;
    a non-transitory computer readable medium storing instructions executable by a computer processor, the instructions comprising functionality for:
        obtaining from the measurement device a plurality of physical property measurements of a sample with an unknown concentration ($C_s$) of a surfactant and of a benchmark solution with a known concentration of the surfactant;
        determining a critical micelle concentration ($C_{cm\ assumed}$) of the sample from the plurality of physical property measurements of the sample and based on an assumed surfactant concentration ($C_{assumed}$) of the sample;
        determining an actual critical micelle concentration ($C_{cm}$) of the surfactant in the benchmark solution from the plurality of physical property measurements of the benchmark solution; and
        calculating the unknown concentration ($C_s$) of the surfactant in the sample from the following equation: $C_s = C_{cm} / (C_{cm\ assumed} / C_{assumed})$; and
    at least one input device connected to the computer processor.

2. The device according to claim 1, further comprising a concentration fluid chamber.

3. The device according to claim 1, wherein the instructions further comprise functionality for generating a control signal for the measurement device to dilute the sample and the benchmark solution when taking the plurality of physical property measurements of the sample and of the benchmark solution.

4. The device according to claim 3, wherein the instructions to dilute comprise instructions to add an amount of dilution fluid at a dilution interval.

* * * * *